United States Patent
Koay et al.

(10) Patent No.: US 11,730,561 B2
(45) Date of Patent: Aug. 22, 2023

(54) APPARATUS AND METHODS FOR THREE-DIMENSIONAL PRINTED ORAL STENTS FOR HEAD AND NECK RADIOTHERAPY

(71) Applicant: Board of Regents, The University of Texas System, Austin, TX (US)

(72) Inventors: Eugene Jon Koay, Houston, TX (US); Caroline Chung, Houston, TX (US); Christopher T. Wilke, Houston, TX (US); Clifton David Fuller, Houston, TX (US); Mohamed Zaid, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 543 days.

(21) Appl. No.: 16/631,662

(22) PCT Filed: Jul. 17, 2018

(86) PCT No.: PCT/US2018/042364
§ 371 (c)(1),
(2) Date: Jan. 16, 2020

(87) PCT Pub. No.: WO2019/018322
PCT Pub. Date: Jan. 24, 2019

(65) Prior Publication Data
US 2020/0170749 A1   Jun. 4, 2020

Related U.S. Application Data

(60) Provisional application No. 62/533,321, filed on Jul. 17, 2017.

(51) Int. Cl.
*G06T 15/00* (2011.01)
*A61B 90/16* (2016.01)
(Continued)

(52) U.S. Cl.
CPC ............... *A61B 90/16* (2016.02); *A61N 5/10* (2013.01); *B33Y 10/00* (2014.12); *B33Y 50/00* (2014.12);
(Continued)

(58) Field of Classification Search
CPC .. A61N 2005/1097; A61N 5/10; B33Y 10/00; B33Y 50/00; B33Y 80/00;
(Continued)

(56) References Cited

U.S. PATENT DOCUMENTS

| 7,234,937 B2 | 6/2007 | Sachdeva et al. |
| 9,402,693 B2 | 8/2016 | Colby |

(Continued)

FOREIGN PATENT DOCUMENTS

| CN | 104043205 | 9/2014 | |
| EP | 3389548 B1 * | 9/2021 | ........... A61C 13/081 |

(Continued)

OTHER PUBLICATIONS

Wilke et al., Design and fabrication of a 3D-printed oral stent for head and neck radiotherapy from routine diagnostic imaging;3D Printing in Medicine 3, Article No. 12 (2017).*

(Continued)

*Primary Examiner* — Phu K Nguyen
(74) *Attorney, Agent, or Firm* — Parker Highlander PLLC (57) ABSTRACT

Apparatus and methods for providing three-dimensional printed oral stents are provided for head and neck radiotherapy. Movement of the jaw of the patient is simulated via a computer processor. Simulating movement of the jaw of the patient comprises rotating and translating a mandible of the jaw. A digital negative impression is transformed into a digital oral stent by adding support structures to the digital negative impression. The support structures facilitate three-dimensional (3D) printing of the patient-specific oral stent.

19 Claims, 9 Drawing Sheets

(51) Int. Cl.
  *B33Y 10/00* (2015.01)
  *B33Y 50/00* (2015.01)
  *B33Y 80/00* (2015.01)
  *A61N 5/10* (2006.01)
  *A61B 6/03* (2006.01)
  *A61C 9/00* (2006.01)

(52) U.S. Cl.
  CPC .............. *B33Y 80/00* (2014.12); *A61B 6/032* (2013.01); *A61C 9/0046* (2013.01); *A61N 2005/1097* (2013.01)

(58) Field of Classification Search
  CPC ..... A61C 9/0046; A61C 19/04; A61C 19/045; A61B 6/03; A61B 90/16; A61B 6/5217; A61B 6/14
  USPC .......................................................... 345/418
  See application file for complete search history.

(56) References Cited

U.S. PATENT DOCUMENTS

| | | | |
|---|---|---|---|
| 10,881,487 B2 * | 1/2021 | Cam ........................ | A61C 7/08 |
| 11,103,330 B2 * | 8/2021 | Webber .................. | B33Y 10/00 |
| 11,318,667 B2 * | 5/2022 | Mojdeh ................. | B29C 64/232 |
| 2006/0003292 A1 | 1/2006 | Lauren et al. | |
| 2009/0209852 A1 | 8/2009 | Mate et al. | |
| 2010/0124731 A1 | 5/2010 | Groscurth et al. | |
| 2013/0066598 A1 | 3/2013 | Fisker et al. | |
| 2013/0296998 A1 | 11/2013 | Leotta et al. | |
| 2015/0094838 A1 | 4/2015 | Mac Laverty | |
| 2015/0142159 A1 | 5/2015 | Chang | |
| 2016/0093100 A1 | 3/2016 | Gyu et al. | |
| 2016/0129637 A1 | 5/2016 | Zhou et al. | |
| 2016/0256709 A1 | 9/2016 | Robar et al. | |
| 2016/0256711 A1 | 9/2016 | Pappas et al. | |
| 2016/0271379 A1 | 9/2016 | Pouliot et al. | |
| 2016/0279445 A1 | 9/2016 | Ju | |
| 2016/0310259 A1 | 10/2016 | Assmann et al. | |
| 2017/0105816 A1 * | 4/2017 | Ward ..................... | A61C 7/146 |
| 2019/0000599 A1 * | 1/2019 | Hanuschik ........... | A61C 15/047 |
| 2021/0220087 A1 * | 7/2021 | Kopelman .............. | B29C 64/10 |
| 2022/0027526 A1 * | 1/2022 | Ruedisueli ............. | A46B 11/06 |

FOREIGN PATENT DOCUMENTS

| | | |
|---|---|---|
| JP | 2010-142491 | 7/2010 |
| RU | 2504344 | 1/2014 |
| WO | WO-2016029109 A2 * | 2/2016 ............ A61F 7/007 |
| WO | WO 2016-044352 | 3/2016 |
| WO | WO-2021225916 A2 * | 11/2021 ............ A61F 7/007 |

OTHER PUBLICATIONS

Liang K, Carmone S, Brambilla D, Leroux JC. 3D printing of a wearable personalized oral delivery device: A first-in-human study. Science advances. May 9, 2018;4(5):eaat2544.*
Schweiger J, Edelhoff D, Guth JF. 3D Printing in Digital Prosthetic Dentistry: An Overview of Recent Developments in Additive Manufacturing. Digital Workflows and Material Sciences in Dental Medicine. 2021;10:99.*
Wilke et al., "Design and fabrication of a 3D-printed oral stent for head and neck radiotherapy from routine diagnostic imaging," *3D Printing in Medicine*, 3:12, 2017.
Zaid et al., "A prospective parallel design study testing non-inferiority of customized oral stents made using 3D printing or manually fabricated methods," *Oral Oncology*, 106:104665, 2020.
Zaid et al., "Creating customized oral stents for head and neck radiotherapy using 3D scanning and printing," *Radiation Oncology*, 14:148, 2019.
Chan et al., "3D Rapid Prototyping for Otolaryngology—Head and Neck Surgery: Applications in Image-Guidance, Surgical Simulation and Patient-Specific Modeling," PLoS One, 10(9):e0136370, 2015.
Ionita, "3D printing: custom patient treatment becomes a reality," retrieved from http://blog.stratasys.com/2015/11/24/3d-printed-brain-vessel-models/, 2015.
Mitsouras et al., "Medical 3D Printing for the radiologist," *Radiographics*, 35(7):1965-1988, 2015.
PCT International Preliminary Report on Patentability issued in International Application No. PCT/US2018/042364, dated Jan. 30, 2020.
PCT International Search Report and Written Opinion issued in International Application No. PCT/US2018/042364, dated Nov. 5, 2018.
Ripley et al., "3D printing from MRI data: harnessing strengths and minimizing weaknesses," *Journal of Magnetic Resonance Imaging*, 45(3):635-645, 2017.
Rubenfire, "Radiologists look toward future in 3-D printing," retrieved from https://www.modernhealthcare.com/article/20161126/MAGAZINE/311269950/radiologists-look-toward-future-in-3-d-printing, 2016.
Johnson et al., "Fabrication of customized tongue-displacing stents: Considerations for use in patients receiving head and neck radiotherapy," *JADA*, 2013; 144(6):594-600.

* cited by examiner

FIG. 13

APPARATUS AND METHODS FOR THREE-DIMENSIONAL PRINTED ORAL STENTS FOR HEAD AND NECK RADIOTHERAPY

CROSS-REFERENCE TO RELATED APPLICATIONS

This application is a national phase application under 35 U.S.C. § 371 of International Application No. PCT/US2018/042364, filed Jul. 17, 2018, which claims priority to U.S. Provisional Patent Application Ser. No. 62/533,321 filed Jul. 17, 2017, the entire contents of each of which are incorporated herein by reference.

BACKGROUND INFORMATION

There are an estimated fifty thousand new cases of head and neck cancer diagnosed in the United States each year and over ten times that number of cases globally. The majority of these patients will receive radiotherapy at some point in their treatment course as either definitive or adjuvant therapy. Significant toxicities of head and neck radiotherapy are mucositis and dysgeusia (change in taste) due to irradiation of the oral mucosa, including the tongue, hard palate, gums, and other structures of the oral cavity and oropharynx. One method to reduce these toxicities is the physical displacement of adjacent tissues away from the tumor using oral stents.

Unfortunately, most radiation oncology practices do not use custom, patient-specific oral stents because it requires significant resource investments on the part of the local dental specialists and patients. Some estimates of the costs for patient-specific oral stents exceed $2,500 per device. Further compounding this problem is that many community dentists do not have specific training in the creation of these stents for radiotherapy treatment. Given the significant time investment required to fabricate these devices, there is a relatively low reimbursement to the dental practice compared to other dental procedures. However, the benefits afforded by patient-specific oral stents (e.g. reduced irradiation of the oral mucosa) can outweigh the associated costs if more efficient methods of manufacturing were available.

In addition, oral mucositis is notably observed in patients receiving radiation therapy involving the oral cavity. This significantly painful toxicity can compromise a patient's nutrition, oral hygiene and increase the risk for local and systemic infection. It is a complication that might alter and limit therapeutic options and affect long-term health. Hence, radiation techniques and oral care protocols have been developed to minimize these side effects. The current standard of care includes aggressive oral hygiene, reactive oxygen species inhibitors, growth factors and topical agents to remedy oral mucositis. However, little attention has been paid to minimizing mucositis during the radiation treatment. Previous studies showed how cryotherapy can reduce mucosal susceptibility to damage from chemotherapy through induced mucosal vasoconstriction.

Accordingly, a need exists for custom oral stents that address the shortcomings in current methods and devices.

SUMMARY

As explained in more detail below, exemplary embodiments of the present disclosure enable improvements in many aspects of individualized patient-specific oral stents as compared to current devices and methods.

Exemplary embodiments of the present disclosure include an affordable, time saving, and comprehensive solution to achieve patient-specific oral stents using an integrated workflow that uses diagnostic imaging, mathematical modeling, and three-dimensional printing technologies. Results show that oral stents can be manufactured via three-dimensional printing within a few hours. This process does not require any direct patient interaction (other than obtaining a diagnostic or intraoral scan or dental impression) and achieves results comparable to oral stents that typically require at least seventy-two hours to make.

Exemplary embodiments of the process use FDA-approved materials and are anticipated to be reimbursed the same as those that are made without 3D printing technologies. Application of the technology would be expected to increase the utilization of the device by radiation oncologists for their head and neck cancer patients, disrupt the current market for making oral stents that currently use bite molds and other antiquated methods (e.g., cork and tongue blades), and significantly improve outcomes for patients by reducing oral mucositis acutely and associated late toxicities from radiotherapy.

Exemplary embodiments include a method of manufacturing a patient-specific oral stent for head and neck radiotherapy, where the method comprises: segmenting a bony anatomy of an oral cavity of a patient; simulating movement of a jaw of the patient; opening the jaw to a specified distance between a top reference point and a bottom reference point; creating a digital negative impression of the bony anatomy when the jaw is opened to the specified distance; transforming the digital negative impression into a digital oral stent; translating the digital oral stent into a printable file; and printing the printable file via a three-dimensional (3D) printer to create the patient-specific oral stent.

Certain embodiments further comprise forming a cavity in the patient-specific oral stent. Particular embodiments further comprise filling the cavity with fluid and sealing the cavity. Some embodiments further comprise reducing the temperature of the stent and the fluid in the cavity. Specific embodiments further comprise incorporating a fiducial marker into the stent. In certain embodiments, incorporating fiducial markers into the stent comprises forming a cavity in the stent and inserting a rod into the cavity. In particular embodiments, the rod is a radio-opaque rod, and in specific embodiments the rod is a stainless steel rod.

In certain embodiments, segmenting the bony anatomy of the oral cavity of the patient comprises analysis of computed tomography (CT) images. In particular embodiments, segmenting the bony anatomy of the oral cavity of the patient comprises imaging with an intraoral scanner. In some embodiments, segmenting the bony anatomy of the oral cavity of the patient comprises analysis of photographs from a model of a dentition of the patient. In specific embodiments, the top reference point is a top incisor and the bottom reference point is a bottom incisor. In certain embodiments, the top reference point is a top gum and the bottom reference point is a bottom gum. In particular embodiments, the specified distance is between 10 and 25 mm, or between 15 and 22 mm. In some embodiments, the specified distance is approximately 20 mm.

In specific embodiments, movement of the jaw of the patient is simulated via a computer processor. In certain embodiments, simulating movement of the jaw of the patient comprises rotating and translating a mandible of the jaw. In particular embodiments, transforming the digital negative impression into the digital oral stent comprises adding support structures to the digital negative impression. In some embodiments, the support structures facilitate three-dimensional (3D) printing of the patient-specific oral stent. In specific embodiments, transforming the digital negative impression into the digital oral stent comprises adding tissue-displacing surfaces to the digital negative impression. In certain embodiments, the tissue-displacing surfaces comprise a surface configured to displace tissues of the oral cavity and adjacent structures.

In some embodiments, the patient-specific oral stent comprises a plurality of materials. In specific embodiments, the plurality of materials comprises a first material having a first hardness and a second material having a second hardness, wherein the first hardness is greater than the second hardness. In certain embodiments, the plurality of materials comprises an acrylic resin and a thermoplastic material that is softer than the acrylic resin.

In particular embodiments, the patient-specific oral stent comprises a body portion; the patient-specific oral stent comprises occlusal surfaces that contact teeth of a patient when inserted into the oral cavity of the patient; the body portion is formed from the acrylic resin; and the occlusal surfaces are formed from the thermoplastic material. Some embodiments further comprise: heating the patient-specific oral stent; placing the patient-specific oral stent into the oral cavity of the patient; and instructing the patient to bite down on the patient-specific oral stent. In specific embodiments, the plurality of materials comprises a first material of a first color and a second material of a second color, wherein the first color is different than the second color.

Certain embodiments include a patient-specific oral stent for head and neck radiotherapy manufactured according to the methods disclosed herein. Exemplary embodiments include a patient-specific oral stent for head and neck radiotherapy comprising: a first material having a first hardness; and a second material having a second hardness, wherein the first hardness is greater than the second hardness. In particular embodiments, the first material is an acrylic resin and the second material is a thermoplastic material. In specific embodiments, the patient-specific oral stent comprises a body portion; the patient-specific oral stent comprises occlusal surfaces that contact teeth of a patient when inserted into the oral cavity of the patient; the body portion is formed from the acrylic resin; and the occlusal surfaces are formed from the thermoplastic material.

Certain embodiments further comprise a fiducial marker. In particular embodiments, the fiducial marker comprises a rod inserted into a cavity. In some embodiments the rod is a radio-opaque rod, and more particularly, a stainless steel rod. Specific embodiments further comprise a cavity with an opening, and a plug configured to seal the opening. Certain embodiments further comprise fluid in the cavity, and in particular embodiments, the fluid has a temperature less than 50 degrees.

Certain embodiments include a patient-specific oral stent for head and neck radiotherapy comprising: a cavity comprising an opening, and a removable plug, where the cavity is configured to contain a fluid, and the removable plug is configured to seal the opening of the cavity. Some embodiments further comprise a fluid in the cavity, and in specific embodiments, the fluid has a temperature less than 50 degrees. Particular embodiments further comprise a fiducial marker, and in certain embodiments the fiducial marker comprises a rod inserted into a cavity. In some embodiments, the rod is a radio-opaque rod.

Certain embodiments include a method of reducing intraoral temperature, where the method comprises: obtaining an oral stent comprising a cavity; placing a fluid into the cavity of the oral stent; and placing the stent into an oral cavity, where the temperature of the fluid is less than the temperature of the oral cavity. Particular embodiments further comprise sealing the cavity with a plug after placing the fluid into the cavity of the oral stent. Certain embodiments further comprise reducing the temperature of the fluid and the stent after the fluid has been placed in the cavity. Some embodiments further comprise reducing the temperature of the fluid prior to placing the fluid into the cavity. In specific embodiments the temperature of the fluid is less than 50 degrees Fahrenheit when the stent is placed into the oral cavity.

In the following, the term "patient-specific" is defined as manufactured or configured with dimensions obtained from a particular patient or individual.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "substantially" and "approximately" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

As shown in FIG. 10, computed tomography (CT) imaging of the stent revealed distinctive visualization of the fiducial markers. The fiducial markers were visualized in the coronal, axial and sagittal views in FIG. 10.

DETAILED DESCRIPTION OF ILLUSTRATIVE EMBODIMENTS

As discussed more fully below, exemplary embodiments of the present disclosure include devices and methods for manufacturing a patient-specific oral stent for head and neck radiotherapy. While the individual aspects of the methods will be described later in further detail, an overview of an exemplary method will be initially presented.

Figure 1:
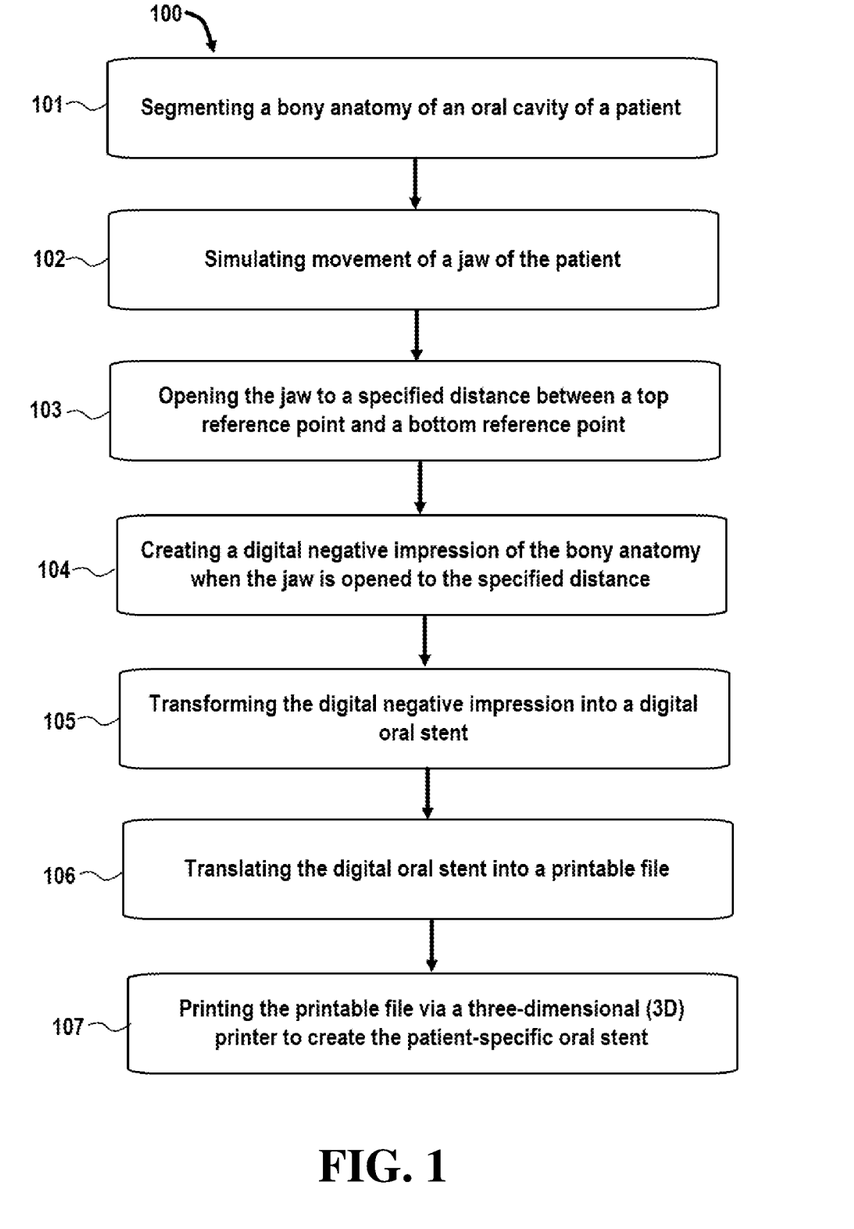
FIG. 1 displays a flowchart of steps in a method of manufacturing a patient-specific oral stent for head and neck radiotherapy according to an exemplary embodiment.

Referring initially to FIG. 1, method 100 for manufacturing a patient-specific oral stent for head and neck radiotherapy comprises a series of steps 101-107. Method 100 includes initially segmenting a bony anatomy of an oral cavity of a patient in step 101. Next, movement of a jaw of the patient is simulated in step 102, and the jaw is opened to a specified distance between a top reference point and a bottom reference point in step 103. A digital negative impression of the bony anatomy can be created when the jaw is opened to the specified distance in step 104. Next, the digital negative impression can be transformed into a digital oral stent in step 105, which can then be translated into a printable file in step 106. Finally, the printable file can be printed via a three-dimensional (3D) printer to create the patient-specific oral stent in step 107.

Figure 2:
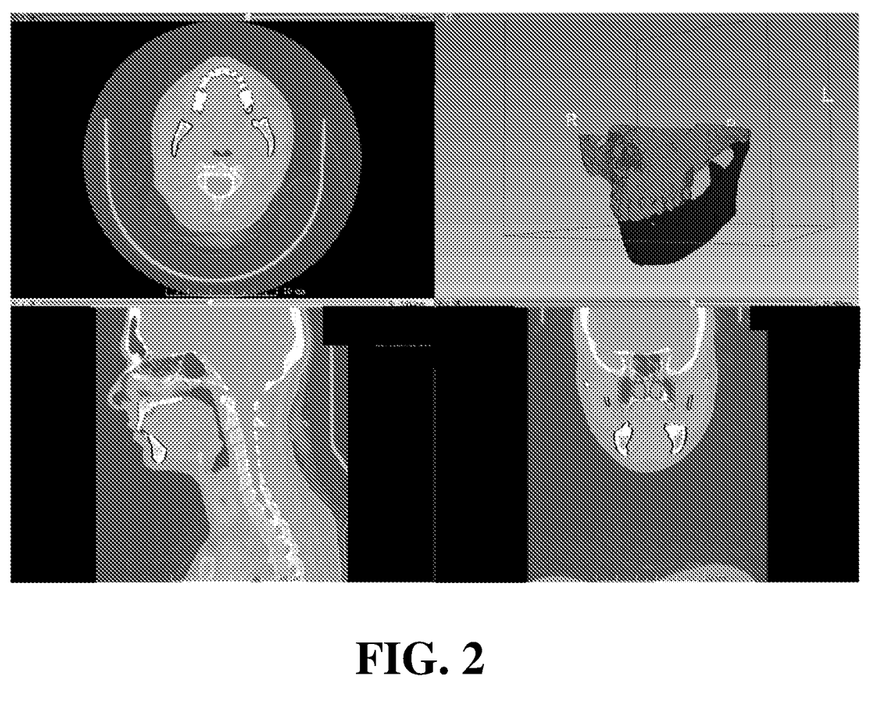
FIG. 2 displays segmentation of the mandible and maxilla from routine diagnostic computed tomography (CT) images according to the embodiment of FIG. 1.
Figure 3:
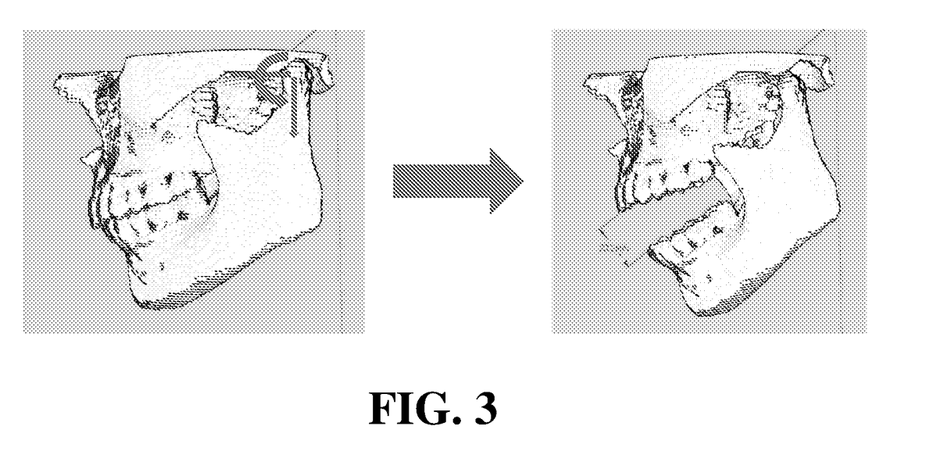
FIG. 3 displays a model created from the segmented dataset using a (computer-aided design) CAD software package according to the embodiment of FIG. 1.

FIG. 2 provides a display of the segmentation of a mandible and maxilla from routine diagnostic computed tomography (CT) images as contemplated in step 101 from FIG. 1. In FIG. 3, a model is created from the segmented dataset using a CAD software package. The mandible can then be rotated and translated to simulate physiologic mouth opening as in steps 102 and 103 of FIG. 1. In particular embodiments, the mandible is rotated and translated using rigid body deformation with the temporomandibular joint (TMJ) set as the axis of rotation. The desired incisal opening is selected individually for each patient based upon the degree of jaw mobility observed and required space clinically to optimally spare normal tissues from radiation exposure. This is typically set at approximately fifty percent of maximal incisal opening and is usually on the order of approximately 10-20 mm, but may be adapted as clinically indicated. Different embodiments may include stents with surfaces providing varying degrees of tongue depression, tongue elevation, tongue lateralization, tongue protrusion, lip protrusion, or buccal mucosal displacement as appropriate.

Figure 4:
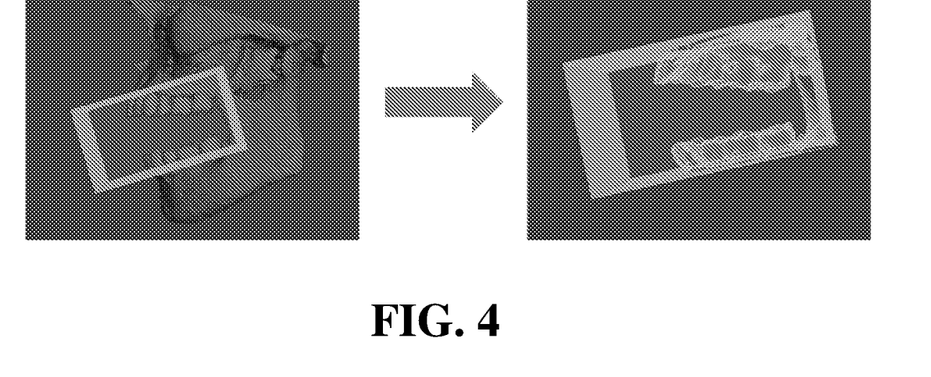
FIG. 4 displays a digital impression of the relationship between the mandibular and maxillary dentition with the simulated jaw opening is created from the CAD model according to the embodiment of FIG. 1.

In FIG. 4, the mandibullomaxillary model created in the previous step is used to create a digital "impression" of the relationship between the maxillary and mandibular dentition as contemplated in step 104 of FIG. 1. In this step, a volumetric block can be created and positioned such that it overlaps with both the mandibular and maxillary dentition. In certain embodiments, Boolean subtraction is performed between the mandibullomaxillary model and block to create a digital negative impression of the dentition positioned with the desired mandibular opening. This "virtual dental impression" is analogous to the physical alginate impression obtained in dental clinic in the creation of an oral stent. FIG. 4 depicts the positioning of the block and Boolean subtraction method used to obtain the digital impression.

Figure 5:
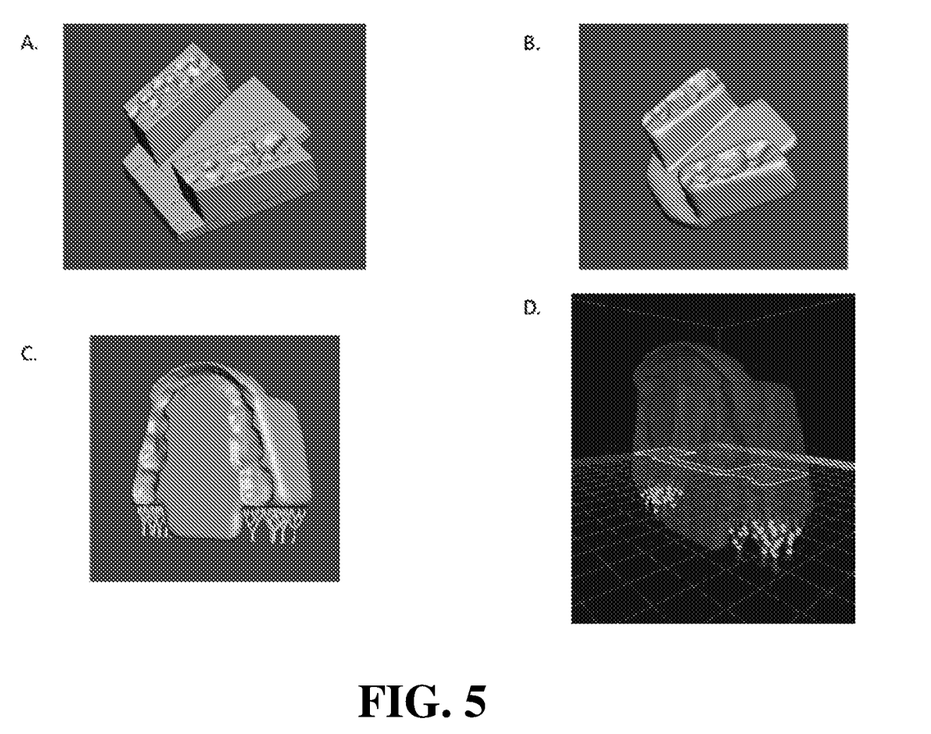
FIG. 5 displays a patient-specific oral stent is created from the digital impression according to the embodiment of FIG. 1.

In FIG. 5, a digital impression is transformed into a digital stent as contemplated in step 105 of FIG. 1. In particular, FIG. 5 panel A shows a digital impression of the relationship between the mandibular and maxillary dentition with the simulated jaw opening is created from the CAD model a. As shown in panel B, in certain embodiments the oral stent geometry is formed from the digital impression block by removing the excess material much in the same fashion as is performed in the dental lab. Once the basic geometry of the stent has been created from the impression block, post-processing steps can be performed to smooth the sharp edges in the model to prevent trauma to the soft tissues when the stent is used clinically. Referring now to panel C, the stent can then be oriented with support structures added as necessary to enable successful 3D printing of the device. The model file can then be inputted into slicing software to translate the model into machine coordinates for 3D printing as shown in panel D.

Figure 6:
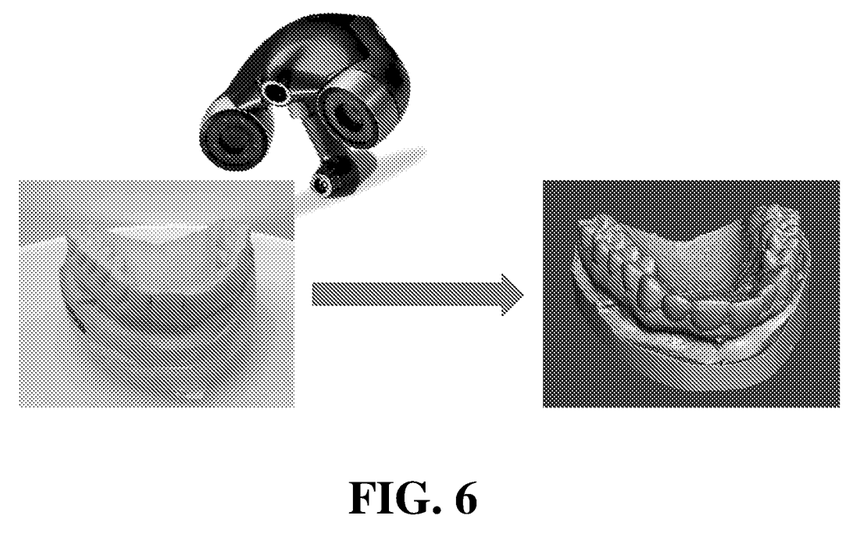
FIG. 6 displays images of a standard dental impression model captured by a commercial 3D scanner (left) and used to create a 3D digital rendering of the model (right) according to the embodiment of FIG. 1.

In addition to CT imaging, digital images of the dentition can be obtained through conventional dental impression models. FIG. 6 illustrates images of a standard dental impression model captured by a commercial 3D scanner (left) and used to create a 3D digital rendering of the model (right). Using this method, standard alginate dental impressions and a bite record are obtained of and used to create a stone dental model with the desired mouth opening. Digital models are created of both the stone maxillary and mandibular dentition using a commercial 3D scanner (FIG. 6).

Figure 7:
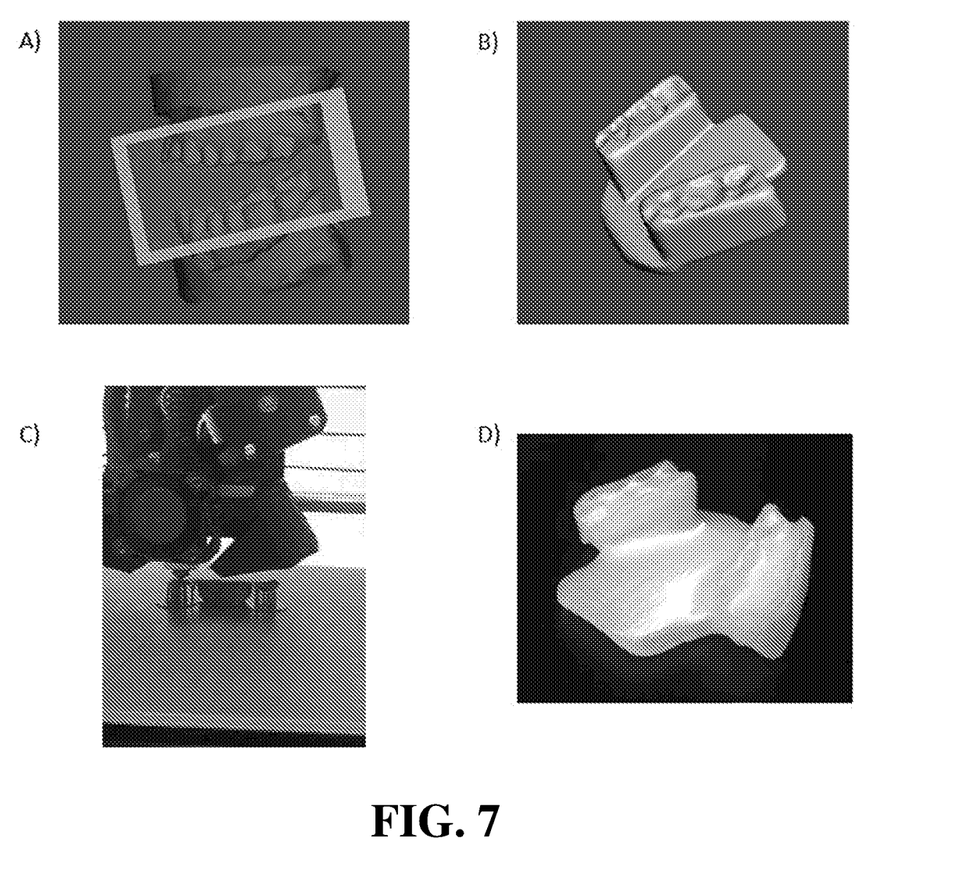
FIG. 7 displays a digital impression created from 3D-scanned stone dental models according to the embodiment of FIG. 1.

In certain embodiments, digital images of the dentition can be obtained directly using an intraoral scanner. One commercial embodiment of such an intraoral scanner is available at www.itero.com. Once a digital scan of the dentition is made with the intraoral scanner, a "virtual" stone dental model can be made, and the process would follow the same subsequent steps. The digital versions of the dental stone models can then be imported into the CAD software similar to the models obtained from the CT images. The digital versions can then be manipulated to achieve the incisal opening and orientation as measured by the bite record obtained in the dental clinic. The digital "impression" and subsequent creation of the oral stent is performed in the same manner as described previously. In FIG. 7 panel A, a digital impression is created from 3D-scanned stone dental models. Panel B of FIG. 7 shows the stent is digitally designed to conform to the dental anatomy. FIG. 7 panel C illustrates 3D printing of the oral stent as contemplated in step 107 of FIG. 1. FIG. 7 panel D shows the oral stent following post-processing and removal of support structures. The file containing the oral stent model can be exported using a stereolithography file format (.stl) which is an industry standard used for 3D printing applications. Using this file format, the stent can be fabricated on nearly any 3D printer using a biocompatible FDA-approved material.

Figure 8:
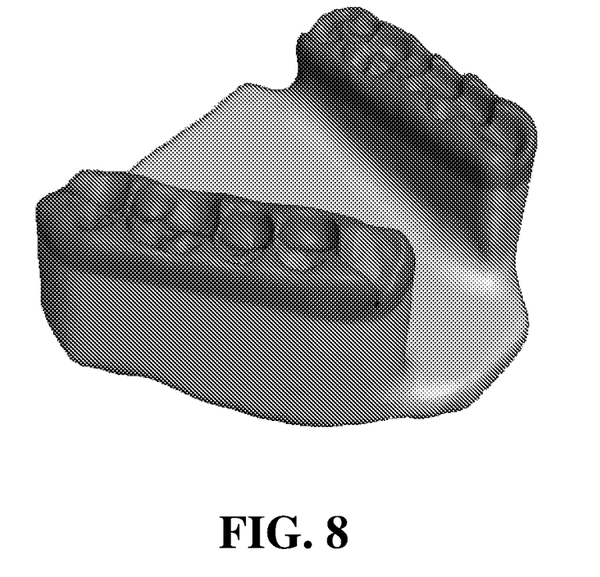
FIG. 8 displays a multi-material 3D printed stent according to the embodiment of FIG. 1.

FIG. 8 illustrates an example of a multi-material 3D printed patient-specific stent. The body portion of the stent (shown in light gray) could be fabricated out of a hard polymer while the occlusal surfaces (shown in dark gray) could be fabricated from a thermoplastic material which would conform to the patient's dentition.

Next generation 3D printers have begun to incorporate the ability to print with multiple materials incorporated into a single object. The advantage of multi-material printing is both cosmetic (printing with multi-colored materials) as well as functional (creating objects with varying material properties). While certain embodiments of stents may be fabricated out of a single polymer, e.g. either biocompatible polylactic acid (PLA) or FDA-approved dental resins, other embodiments may include a plurality of materials.

Particular stent embodiments may contain two materials: the body would be fabricated out of a hard acrylic-resin or similar polymer while the occlusal surfaces which come into contact with the teeth would be fabricated from a softer thermoplastic material. The advantages of using a thermoplastic material for the occlusal surfaces of the stent include patient comfort and ease of fabrication. Modeling and 3D printing of the small details of the occlusal surfaces can be challenging and if not performed correctly can lead to poorly fitting stents that can cause significant patient discomfort.

Printing the occlusal surfaces from a softer thermoplastic material would allow the occlusal surfaces to be formed precisely from the patient's dentition by heating the stent and having the patient bite into the device to create an impression in the material that would harden as the stent cooled. The rationale for not printing the entire stent in the thermoplastic material is due to concern that the stent would lack sufficient structural support to ensure a rigid fixation of the jaw position during the course of the radiotherapy treatment. By creating the stent with dual materials, it may be possible to incorporate both the rigidity necessary for the stent to properly function as designed as well as for improved patient comfort and tolerance of the device.

Certain embodiments may include other materials to help reduce mucositis, including for example silver nitrate. Particular embodiments may incorporate a radiopaque material into the design and construction of the stent which could be used for visualization during set-up to confirm correct positioning of the patient and device.

Figure 9:
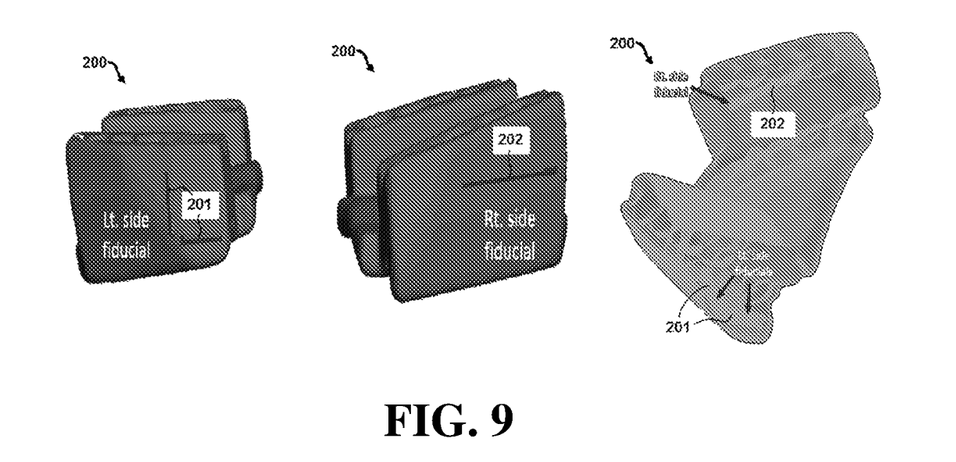
FIG. 9 displays multiple views of an exemplary embodiment of a stent comprising a fiducial marker.

Certain embodiments may also comprise fiducial markers to serve as reference points during imaging procedures. For example, FIG. 9 shows multiple views of a stent 200 comprising a first fiducial marker 201 on the left side and a second fiducial marker 202 on the right side of the stent. In the particular embodiment shown, the fiducial markers can be formed by creating a cavity in stent 200 and inserting a rod in the cavity (e.g. stainless steel or other suitable radio-opaque material capable of being visualized during an imaging procedure). In the specific embodiment of FIG. 9, first fiducial marker 201 comprises two stainless steel rods (approximately 2 mm in diameter) cemented into perpendicular cavities that are approximately 10×2×5 mm below the occlusal surface of tooth number 15 (left second molar). In addition, the embodiment shown in FIG. 9 has fiducial marker 202 comprising a single stainless steel rod inserted into a cavity that is approximately 25×2×5 mm on the right lateral surface, just below the occlusal surface level of teeth number 3, 4 and 5 (right first and second premolar and first molar).

Figure 10:
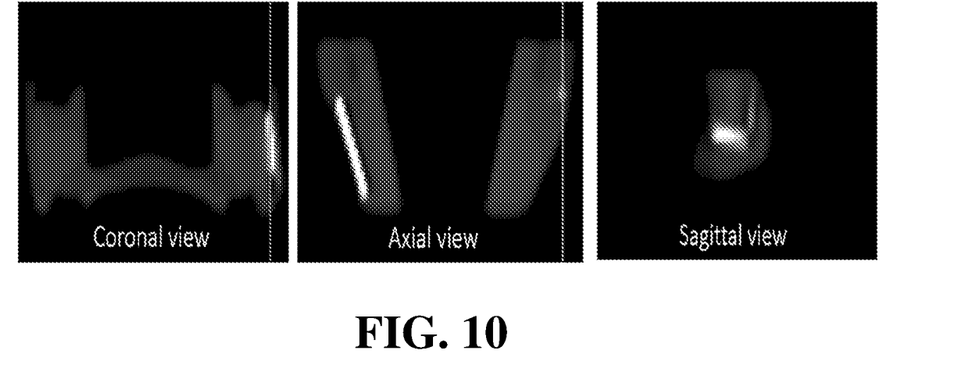
FIG. 10 displays coronal, axial and sagittal views of computed tomography (CT) imaging of the embodiment of FIG. 9.
Figure 11:
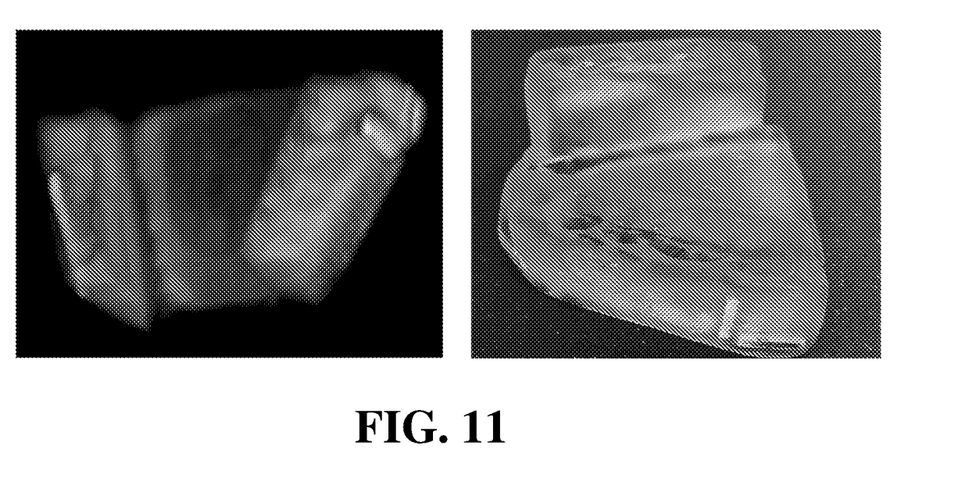
FIG. 11 illustrates a CT scan of the stent on the left and a photograph of the stent on the right showing the fiducial markers FIG. 11 displays a CT scan on the left and a photograph on the right of the embodiment of FIG. 9.

As shown in FIG. 10, computed tomography (CT) imaging of the stent revealed distinctive visualization of the fiducial markers. The fiducial markers were visualized in the coronal, axial and sagittal views in FIG. 10. FIG. 11 illustrates a CT scan of the stent on the left and a photograph of the stent on the right showing the fiducial markers.

Figure 12:
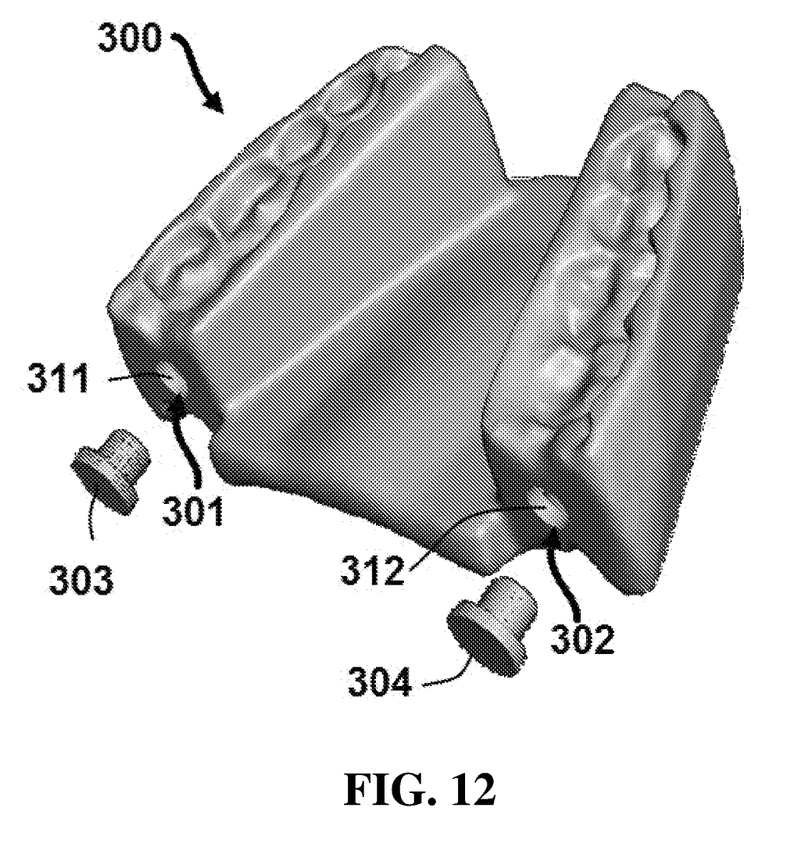
FIG. 12 displays a perspective view of an exemplary embodiment of a stent configured to contain cooling fluid.

In addition, certain embodiments of the present disclosure may comprise stents with one or more cavities configured to contain cooling fluid. Referring now to FIG. 12, a stent 300 comprises a first cavity 301 and a second cavity 302. In this embodiment, first cavity 301 has a first opening 311 on the posterior surface of the stent, while second cavity 302 has a second opening 312, also on the posterior surface of the stent. The embodiment shown also comprises removable plugs 303 and 304 configured to seal first and second openings 311 and 312 of cavities 301 and 302, respectively. In certain embodiments, plugs 303 and 304 may be 3D printed.

Cavities 301 and 302 can be filled with a fluid that serves as a cooling agent to reduce temperature increases of stent 300 during use because the temperature of the fluid is less than the temperature of the oral cavity in which the stent is placed. This can significantly reduce radiation-induced mucositis while enabling the maximum dose delivery, providing a significant positive impact on patient's quality of life. In certain embodiments, the fluid can be reduced to temperatures significantly below temperatures in the oral cavity. For example, the fluid may be reduced to temperatures of less than 80, 70, 60, 50, 40, or 30 degrees Fahrenheit in certain embodiments.

To demonstrate the cooling effects of the fluid-filled cavities, temperature data was obtained for three stents, including the embodiment shown in FIG. 12. In particular, cavities 301 and 302 were filled with mineral water, but it is understood that other fluids can be used in other embodiments. Openings 311 and 312 were then sealed with plugs 303 and 304. As a control, two solid 3D printed stents were also manufactured for the same volunteer. The fluid filled stent (FFS) and one of the solid stents (standard A) were frozen for 2 hours, while the third solid stent (standard B) was left at the room temperature. To measure the cooling effect of the different stents, each stent was placed for 21 minutes into the volunteer's mouth, and the oral temperature was recorded every 3 minutes. A graph of the different temperatures is shown in FIG. 13.

Figure 13:
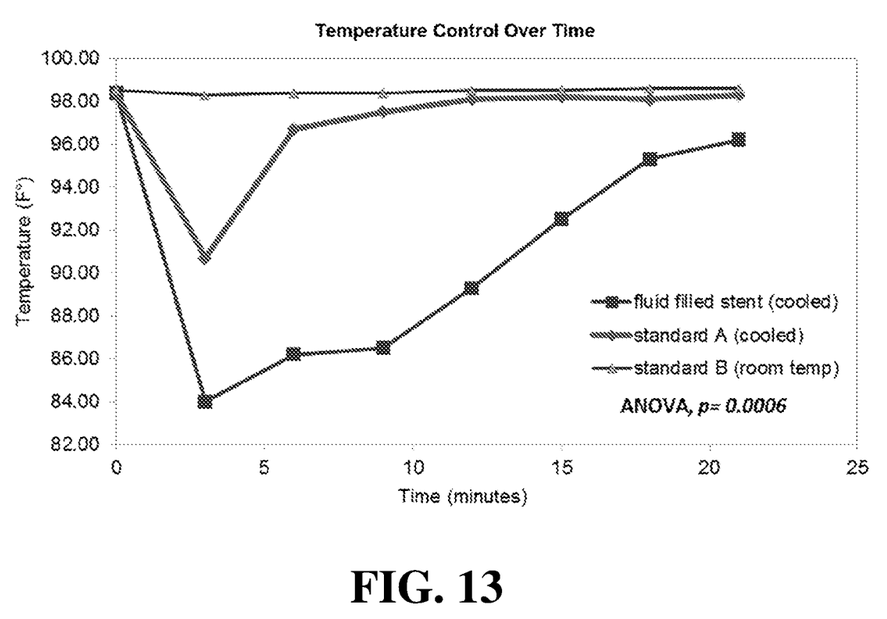
FIG. 13. displays temperature data for the embodiment of FIG. 12 as compared to other stents that do not include cooling fluid.

As shown in FIG. 13, both the FFS and Standard A stents exhibited an initial drop in the temperature by the second time point. However, the FFS showed a more significant drop in temperature when compared to Standard A. In addition, the FFS showed a longer lasting cooling effect and a gradual rise in the intraoral temperature when compared to the Standard A, which was more abrupt. Furthermore, the Standard B stent did not show any significant impact on the recorded intraoral temperature. The recorded differences were statistically significant, with an analysis of variance (ANOVA) p less than 0.004. This data indicates that a stent with a cavity filled with cooled fluid can significantly reduce intraoral temperatures and minimize radiation-induced mucositis.

All of the devices, apparatus, systems and/or methods disclosed and claimed herein can be made and executed without undue experimentation in light of the present disclosure. While the devices, apparatus, systems and methods of this invention have been described in terms of particular embodiments, it will be apparent to those of skill in the art that variations may be applied to the devices, apparatus, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
US20160310259
US20130296998
US20160271379
WO2016044352
US20160093100
US20100124731
U.S. Pat. No. 9,402,693
US20160256711
US20160256709
US20160279445
US20150094838
US20160129637

Jemal A, Bray F, Center M M, Ferlay J, Ward E, Forman D. Global cancer statistics. C A Cancer J Clin. 2011; 61(2):69-90. doi:10.3322/caac.20107.

Ward M C, Ross R B, Koyfman S A, et al. Modern Image-Guided Intensity-Modulated Radiotherapy for Oropharynx Cancer and Severe Late Toxic Effects. JAMA Otolaryngol Neck Surg. 2016; 142(12):1164. doi:10.1001/jamaoto.2016.1876.

Franzese C, Fogliata A, Clerici E, et al. Toxicity profile and early clinical outcome for advanced head and neck cancer patients treated with simultaneous integrated boost and volumetric modulated arc therapy. Radiat Oncol. 2015; 10(1):224. doi:10.1186/s13014-015-0535-0.

Blanchard P, Garden A S, Gunn G B, et al. Intensity-modulated proton beam therapy (IMPT) versus intensity-modulated photon therapy (IMRT) for patients with oropharynx cancer? A case matched analysis. Radiother Oncol. 2016; 120(1):48-55. doi:10.1016/j.radonc.2016.05.022.

Wang X, Hu C, Eisbruch A. Organ-sparing radiation therapy for head and neck cancer. Nat Rev Clin Oncol. 2011; 8(11):639-648. doi:10.1038/nrclinonc.2011.106.

Dirix P, Nuyts S. Evidence-based organ-sparing radiotherapy in head and neck cancer. Lancet Oncol. 2010; 11(1):85-91. doi:10.1016/S1470-2045(09)70231-1.

Johnson B, Sales L, Winston A, Liao J, Laramore G, Parvathaneni U. Fabrication of customized tongue-displacing stents: considerations for use in patients receiving head and neck radiotherapy. J Am Dent Assoc. 2013; 144(6):594-600. http://www.ncbi.nlm nih.gov/pubmed/23729456.

Kaanders J H, Fleming T J, Ang K K, Maor M H, Peters U. Devices valuable in head and neck radiotherapy. Int J Radiat Oncol. 1992; 23(3):639-645. http://www.ncbi.nlm nih.gov/pubmed/1612965.

Nayar S, Brett R, Clayton N, Marsden J. The Effect of a Radiation Positioning Stent (RPS) in the Reduction of Radiation Dosage to the Opposing Jaw and Maintenance of Mouth opening after Radiation Therapy. Eur J Prosthodont Restor Dent. 2016; 24(2):71-77. http://www.ncbi.nlm nih-.gov/pubmed/27424338.

Verrone J R, Alves F de A, Prado J D, et al. Impact of intraoral stent on the side effects of radiotherapy for oral cancer. Head Neck. 2013; 35(7):E213-E217. doi:10.1002/hed.23028.

Medical 3D Printing for the Radiologist, Mitsouras et al.; retrieved from: https://www.ncbi.nlm nih.gov/pmc/articles/PMC4671424/

Patient-Specific Modeling, Chan et al.; retrieved from: https://www.ncbi.nlm.nih.gov/pmc/articles/PMC4557980/

3D Printing Radiology, Rubenfire, Adam; retrieved from: http://dialog.proquest.com/professional/docview/1845013568/1585BBB8A794C1D6296/4?accountid=157282

Custom Patient Treatment, 3D Printing: Custom Patient Treatment Becomes a Reality, Ionita; retrieved from: http://blog.stratasys.com/2015/11/24/3D-printed-brain-vessel-models/

MRI Data, 3D printing from MRI Data: Harnessing strengths and minimizing weaknesses, Ripley et al.; retrieved from: http://onlinelibrary.wiley.com/wo11/doi/10.1002/jmri.25526/abstract

The invention claimed is:

1. A method of manufacturing a patient-specific oral stent for head and neck radiotherapy, the method comprising:
segmenting a bony anatomy of an oral cavity of a patient;
simulating movement of a jaw of the patient;
opening the jaw to a specified distance between a top reference point and a bottom reference point;
creating a digital negative impression of the bony anatomy when the jaw is opened to the specified distance;
transforming the digital negative impression into a digital oral stent, wherein transforming the digital negative impression into the digital oral stent comprises adding tissue-displacing surfaces to the digital negative impression and wherein the tissue-displacing surfaces comprise a surface configured to provide tongue lateralization;
translating the digital oral stent into a printable file; and
printing the printable file via a three-dimensional (3D) printer to create the patient-specific oral stent.

2. The method of claim 1 further comprising forming a cavity in the patient-specific oral stent.

3. The method of claim 2 further comprising filling the cavity with fluid and sealing the cavity and reducing the temperature of the stent and the fluid in the cavity.

4. The method of claim 1 further comprising incorporating a fiducial marker into the stent.

5. The method of claim 4 wherein incorporating fiducial markers into the stent comprises:
forming a cavity in the stent; and
inserting a rod into the cavity.

6. The method of claim 1 wherein segmenting the bony anatomy of the oral cavity of the patient comprises analysis of computed tomography (CT) images.

7. The method of claim 1 wherein segmenting the bony anatomy of the oral cavity of the patient comprises imaging with an intraoral scanner.

8. The method of claim 1 wherein segmenting the bony anatomy of the oral cavity of the patient comprises analysis of photographs from a model of a dentition of the patient.

9. The method of claim 1 wherein the top reference point is a top incisor and the bottom reference point is a bottom incisor.

10. The method of claim 1 wherein the top reference point is a top gum and the bottom reference point is a bottom gum.

11. The method of claim 1 wherein the specified distance is between 10 and 25 mm.

12. The method of claim 1 wherein the specified distance is approximately 20 mm.

13. The method of claim 1 wherein movement of the jaw of the patient is simulated via a computer processor.

14. The method of claim 1 wherein simulating movement of the jaw of the patient comprises rotating and translating a mandible of the jaw.

15. The method of claim 1 wherein transforming the digital negative impression into the digital oral stent comprises adding support structures to the digital negative impression.

16. The method of claim 15 wherein the support structures facilitate three-dimensional (3D) printing of the patient-specific oral stent.

17. The method of claim 1 wherein:
the patient-specific oral stent comprises a plurality of materials;
the plurality of materials comprises a first material having a first hardness and a second material having a second hardness, wherein the first hardness is greater than the second hardness;
the plurality of materials comprises an acrylic resin and a thermoplastic material that is softer than the acrylic resin;
the patient-specific oral stent comprises a body portion;
the patient-specific oral stent comprises occlusal surfaces that contact teeth of a patient when inserted into the oral cavity of the patient;
the body portion is formed from the acrylic resin; and
the occlusal surfaces are formed from the thermoplastic material.

18. The method of claim 17 further comprising:
heating the patient-specific oral stent;
placing the patient-specific oral stent into the oral cavity of the patient; and
instructing the patient to bite down on the patient-specific oral stent.

19. A method of reducing intraoral temperature, the method comprising:
obtaining an oral stent comprising a cavity;
placing a fluid into the cavity of the oral stent; and
placing the stent into an oral cavity, wherein the temperature of the fluid is less than the temperature of the oral cavity.

* * * * *